(12) United States Patent
Mullens et al.

(10) Patent No.: US 11,141,278 B2
(45) Date of Patent: Oct. 12, 2021

(54) SURGICAL IMPLANTS COMPRISING GRADED POROUS STRUCTURES

(71) Applicant: VITO NV, Mol (BE)

(72) Inventors: Steven Mullens, Mol (BE); Lidia Protasova, Mol (BE); Simge Danaci, Grenoble (FR); Dirk Vangeneugden, Mol (BE); Jasper Lefevere, Mol (BE)

(73) Assignee: VITO NV, Mol (BE)

( * ) Notice: Subject to any disclaimer, the term of this patent is extended or adjusted under 35 U.S.C. 154(b) by 0 days.

(21) Appl. No.: 16/497,758

(22) PCT Filed: Mar. 29, 2018

(86) PCT No.: PCT/EP2018/058245
§ 371 (c)(1),
(2) Date: Sep. 25, 2019

(87) PCT Pub. No.: WO2018/178313
PCT Pub. Date: Oct. 4, 2018

(65) Prior Publication Data
US 2020/0030102 A1 Jan. 30, 2020

(30) Foreign Application Priority Data
Apr. 13, 2017 (EP) .................................. 17166453

(51) Int. Cl.
*A61F 2/30* (2006.01)
*A61F 2/34* (2006.01)

(52) U.S. Cl.
CPC .................. *A61F 2/30907* (2013.01); *A61F 2002/30006* (2013.01); *A61F 2002/30011* (2013.01); *A61F 2002/30028* (2013.01); *A61F 2002/30769* (2013.01); *A61F 2002/30914* (2013.01); *A61F 2002/30915* (2013.01); *A61F 2002/30971* (2013.01); *A61F 2002/30985* (2013.01); *A61F 2002/348* (2013.01)

(58) Field of Classification Search
CPC combination set(s) only.
See application file for complete search history.

(56) References Cited

U.S. PATENT DOCUMENTS

| 4,280,233 A | 7/1981 | Raab |
| 4,978,355 A | 12/1990 | Frey et al. |

(Continued)

FOREIGN PATENT DOCUMENTS

| CN | 1135321 A | 11/1996 |
| CN | 1665551 A | 9/2003 |

(Continued)

OTHER PUBLICATIONS

Jul. 9, 2018, European Patent Office, International Search Report and Written Opinion in PCT/EP2018/058245, which is the International Application to this U.S. Application.

*Primary Examiner* — Yashita Sharma
(74) *Attorney, Agent, or Firm* — Kolitch Romano LLP

(57) ABSTRACT

A surgical implant may include a porous structure with interconnected pores for ingrowth of bone into the porous structure. The porous structure has an arrangement of fibres which are attached to one another, the fibres being arranged in stacked layers. The porous structure has a surface including different regions having different porosities. A method of making the above surgical implant is also described.

18 Claims, 4 Drawing Sheets

(56) References Cited

U.S. PATENT DOCUMENTS

| | | | |
|---|---|---|---|
| 6,993,406 B1 | 1/2006 | Cesarano, III et al. | |
| 2005/0112397 A1 | 5/2005 | Rolfe et al. | |
| 2005/0254985 A1 | 11/2005 | Chiba et al. | |
| 2011/0144764 A1* | 6/2011 | Bagga ...................... | A61F 2/28 623/23.61 |

FOREIGN PATENT DOCUMENTS

| | | | |
|---|---|---|---|
| CN | 1446109 | A | 10/2003 |
| CN | 201631426 | U | 11/2010 |
| EP | 0189546 | A1 | 8/1986 |
| EP | 1820475 | A1 | 8/2007 |

* cited by examiner

SURGICAL IMPLANTS COMPRISING GRADED POROUS STRUCTURES

TECHNICAL FIELD

The present disclosure is related to surgical implants comprising a scaffold structure for bone ingrowth. In particular, the present disclosure is related to surgical implants of the above kind in which the scaffold structure comprises a graded porosity.

INTRODUCTION

From the review article "Graded/Gradient Porous Biomaterials," by Xigeng Miao and Dan Sun, Materials 2010, 3, 26-47 it is known to use graded porous implants for repairing bone-cartilage complex tissue. The part with larger pore size is implanted into bone for bone ingrowth, whereas the part with smaller pore size is to allow cartilage to grow in. In other words, the graded porous implant can be used to select or promote attachment of specific cell types on and in the implant prior to and/or after implantation. The part for bone ingrowth and the part for cartilage ingrowth can be made of different materials. The gradient of material properties may range from one which is suitable for load bearing to one which is suitable for soft tissue regeneration.

U.S. Pat. No. 4,978,355 describes a metal grid embedded in the contact surface of a plastic implant. An additional anchoring surface for ingress of bone tissue is secured to the embedded grid. The anchoring surface is formed of layers of metal wire which are stacked and secured by sintering.

US 2005/0112397 describes a porous structure having a plurality of stacked bonded sheets. The sheets have a plurality of at least partially overlapping apertures formed therein, produced by perforation. Perforating the sheets to create the apertures allows for obtaining differential porosity within the sheet or from sheet to sheet. Regions of high porosity are separated by regions of lower porosity.

Research has indicated that different levels of porosity and pore size of the scaffold structure have an impact on the amount of bone ingrowth and the mechanical stability of the implant. Dense scaffold structures have good mechanical properties but poor bone ingrowth properties. On the contrary, more porous structures provide good biological performance but have a low mechanical strength. The rate of tissue ingrowth in the porous structure is also dependent on the availability of a large surface area for cells to attach and grow on. It is known that most bone forming cells grow on a substratum surface rather than grow in a suspended manner in the cell culture medium. In this regard, a large pore surface area means that a large bone-material interfacial bonding area can be provided.

Furthermore, interconnected porosity promotes the organisation of vascular canals that can ensure the supply of blood and nutrients for the viability of bone.

SUMMARY

Osseointegration is important for many surgical implants, however it is not easily stimulated and/or controlled. Bone ingrowth and vascularisation strongly depend on macroporosity parameters such as pore size, pore size distribution and pore interconnectivity. In order to optimize mechanical properties and macroporosity, several graded/gradient implants materials have been proposed, particularly using additive manufacturing technologies.

Despite the advances to date, there is still a need in the art of improved scaffold structures for surgical implants. In particular, there is a need of providing such scaffold structures which enhance the promotion of bone ingrowth into the structure, yet allowing sufficient freedom in designing the scaffold structure for optimal mechanical properties. There is a need of providing such implants having improved tissue anchoring capabilities. There is also a need in the art of manufacturing scaffold structures of the above kind in a cost-effective way.

According to a first aspect of the disclosure, there is therefore provided a surgical implant as set out in the appended claims. The surgical implant comprises a porous structure with interconnected pores. The pores have sizes suitable for ingrowth of bone and/or soft tissue into the porous structure. The porous structure comprises an arrangement of fibres which are attached to one another and are arranged in advantageously planar layers, the layers being stacked. According to aspects of the disclosure, the porous structure comprises a surface comprising different regions having different porosities. Advantageously, the arrangement of fibres extends to the surface and determines the different porosities by different arrangements of the fibres in the different regions. Advantageously, the different porosities are determined by (different) interspaces between adjacent or consecutive fibres. The term interspace can but does not necessarily refer to the inter-fibre distance. Rather, the term refers more generally to (the size of) the interstitial voids delimited by fibres. Different parameters may influence the porosity of the arrangement of fibres, such as fibre diameter, inter-fibre distance, stacking factor, fibre orientation, etc.

According to a second aspect of the disclosure, there is provided a method of manufacturing a surgical implant of the above kind as set out in the appended claims. The method comprises the steps of forming fibres in advantageously planar layers which are stacked on top of one another, and connecting the fibres of consecutive layers to one another to obtain a porous structure, e.g. a network of fibres. According to aspects of the disclosure, the method comprises the step of arranging the fibres in proximity of a surface of the porous structure such that the surface comprises different regions having different porosities. Advantageously, the fibres are arranged with different interspaces in different regions of the surface.

BRIEF DESCRIPTION OF THE DRAWINGS

Aspects of the disclosure will now be described in detail with reference to the appended drawings, wherein same reference numerals illustrate same features.

DETAILED DESCRIPTION

For purposes of illustration, aspects of the disclosure will be described in relation to a particular example of an acetabular component of a hip implant. It will however be convenient to note that indicated aspects are readily applicable to other kinds of implants, such as spinal implants, cranial implants, maxillofacial implants and dental implants.

Figure 1:
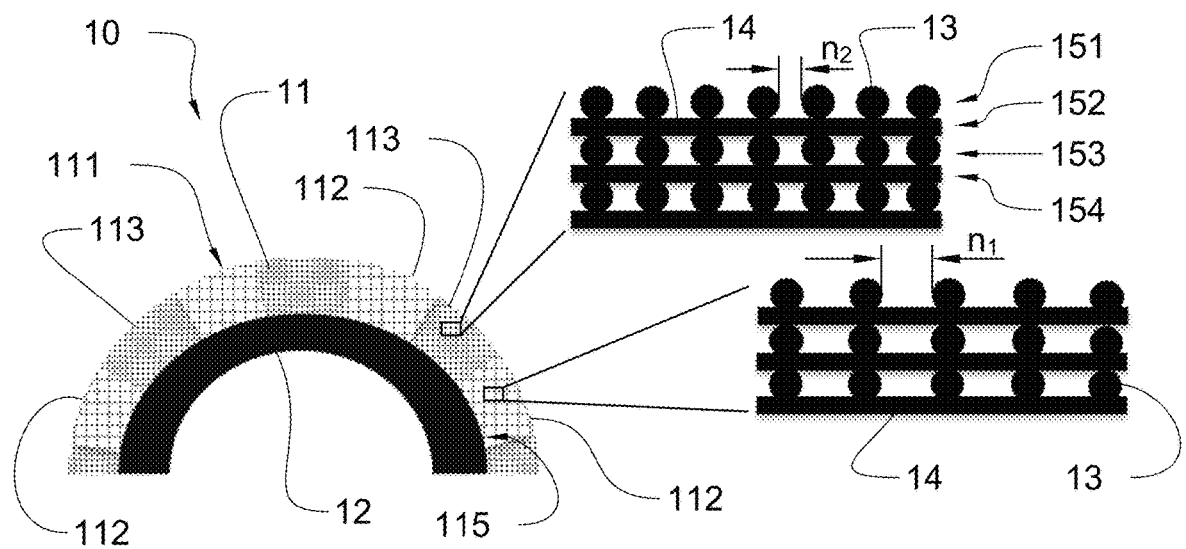
FIG. 1 represents a cross sectional view of an example surgical implant according to aspects of the disclosure invention.

FIG. 1 schematically depicts an implant 10 according to aspects of the disclosure. The implant 10 is shown as an acetabular component of a hip prosthesis and comprises a scaffold part 11. In this particular example, the scaffold part 11 is attached to a dense part 12. The dense part 12 forms a shell of hemispherical shape which may be provided with a liner forming a receiving part of a ball joint. A femoral component of the hip prosthesis (not shown) typically comprises a ball which is accepted in the liner. It will be convenient to note that in other types of implants, the dense part may be omitted.

The scaffold part 11 is a porous structure having interconnected pores which are configured for ingrowth of bone. The scaffold part 11 comprises an external surface 111 forming an interface with the surrounding sound bone structure. Advantageously, the external surface 111 is located opposite surface 115 which forms an interface of attachment to the dense part 12. According to an aspect of the present disclosure, the surface 111 comprises different regions having different porosities. By way of example, the surface 111 comprises first regions 112 and second regions 113. The first regions 112 have a higher volume porosity (determined in a volume contiguous to the surface 111) compared to the second regions 113. In other words, the second regions 113 will have higher density compared to the first regions 112.

According to an aspect, porosity and/or pore size of the first regions 112 and of the second regions 113 can be selected such that the first regions of higher porosity will promote bone ingrowth, while the second regions of lower porosity will promote the ingress of vascular canals into the scaffold structure 11. These vascular canals provide for transport paths for supply of nutrients and cells which further promote bone formation. Therefore, providing on the external surface 111 adjacent regions of higher porosity and lower porosity will provide for parallel paths for ingrowth of bone and vascular canals, and as a result, will enhance the speed with which bone will grow into the scaffold structure 11.

Advantageously, a plurality of the second regions 113 are provided adjacent or in between a plurality of the first regions 112. Advantageously, the first regions 112 and the second regions 113 alternate on the surface 111. The area of extension of the first regions and of the second regions is not particularly limited. Advantageously the first regions and the second regions each extend over an area of at least 4 mm$^2$, advantageously at least 5 mm$^2$, advantageously at least 10 mm$^2$, advantageously at least 20 mm$^2$.

Advantageously, these first and second regions 112, 113 can further extend into the depth of the scaffold structure 11, e.g. until surface 115.

According to an aspect, such a structure 11 with alternating regions of higher porosity and regions of lower porosity is obtained by forming the scaffold structure 11 out of an arrangement of fibres 13, 14. The fibres 13, 14 are disposed in layers 151, 152, 153, 154, etc which are stacked on top of one another, and which are advantageously parallel to one another. This arrangement of fibres extends to the surface 111. Fibres of consecutive layers are attached to one another, and thereby advantageously form a construct which is monolithic, being the scaffold structure 11.

Such monolithic and porous structures can be obtained by well-known additive manufacturing techniques, such as three-dimensional fibre deposition, three-dimensional powder deposition or similar solid free-form fabrication techniques. The fibres or filaments can be extruded as a paste from a nozzle, as is the case with 3D fibre deposition, or can be 3D printed starting from a powder layer which can e.g. be selectively melted (selective laser sintering), or selectively bound with an adhesive (3D printing).

3D fibre deposition (3DFD) (also called robocasting) comprises the extrusion of an advantageously highly viscous paste loaded with metallic or ceramic particles through a thin nozzle. In this case, the paste comprises a powder, such as a metallic or ceramic powder, or a combination of both, an organic binder, optionally a rheology modifier and optionally an anorganic binder, such as a colloidal binder. By computer controlled movement in x, y and z-direction, a porous architecture is built layer-by-layer. The x and y directions typically refer to the plane of the layers 151-154, whereas the z-direction is the direction of stacking of the layers (perpendicular on the plane of the layers). This process can involve multiple nozzles or a single nozzle. The green part which is obtained by the above process can be post-processed in one or two steps: an optional drying step followed by sintering. Sintering may be carried out under vacuum conditions, or in an inert or reducing atmosphere, e.g. to avoid oxidation in case of metals. After sintering, a highly reproducible and periodic porous structure is obtained. The process variables include the nozzle opening (fibre thickness or diameter), the type of nozzle (fibre shape), the inter-fibre distance (pore size) and the stacking of the layers (architecture). The microporosity and surface roughness of the fibres can be controlled. An equipment for 3DFD typically comprises a paste reservoir with nozzle, mounted on an apparatus with numerical control of three or more axes, e.g. an XYZ-table or a CNC machine. Multiple nozzles can be mounted onto the equipment to speed up the production of similar pieces.

Fibres 13, 14 of consecutive layers advantageously extend along transverse directions and the fibres within the same layer are advantageously spaced apart. By way of example, referring to FIG. 1, fibres 13 of layer 151 are parallel to one another and have longitudinal axes cross to the longitudinal axes of fibres 14 in the below layer 152. Fibres 13 and 14 may extend perpendicular to one another, or oblique, e.g. at an angle different from 0° and different from 90°. As a result, a highly porous structure can be obtained. The fibres are advantageously, though not necessarily arranged in an orderly fashion. By way of example, fibres 13 within the same layer can be parallel, extend radially from a common centre, be concentric in circles or extend spirally.

To account for the sometimes complex geometry of surgical implants, the scaffold structures 11 can be made as a block, e.g. by 3DFD as described above, and machined afterwards, e.g. milled, to the correct geometry, e.g. to fit on the dense part 12. The attachment with the dense part 12 can be provided by known techniques, such as sintering, friction welding, laser welding, etc.

Advantageous porous structures 11 may comprise longitudinal channels extending substantially normal to the external surface 111, e.g. the longitudinal channels may extend from the surface 111 in a direction of approach of the interface 115 or the dense part 12. These longitudinal channels may be straight or tortuous. The tortuosity may be defined by staggering the fibres as will be described further below.

According to an aspect, a first porosity gradient may be provided between the first regions 112 and the second regions 113. That is, along a first direction, referred to as gradient direction, the porosity, and therefore also the density of the structure 11, is made to change. The first gradient direction advantageously lies on the surface 111, or may be a direction at least locally tangential to the surface 111.

By way of example, a first region 112 is provided with a porosity P1. A possible adjacent second region 113 is provided with porosity P3, which is different from P1, e.g. P1>P3. Possibly, an intermediate region (not shown) may be interposed between first region 112 and second region 113, which may be provided with porosity P2, with P2 different from P1 and P3. According to an aspect, the porosity changes along the first gradient direction from a higher porosity P1 and hence lower density of the structure 11 in the first region 112 to a lower porosity P3 and hence a higher density of structure 11 in the second region 113. Advantageously, the porosity gradient is one with a porosity decreasing from the first region, possibly through the intermediate region, towards the second region. In other words, P1>P2>P3.

According to yet another aspect, a second porosity gradient may be provided in a direction substantially orthogonal to the first gradient direction, e.g. a direction oriented away from or in approach of the surface 111.

Figure 2:
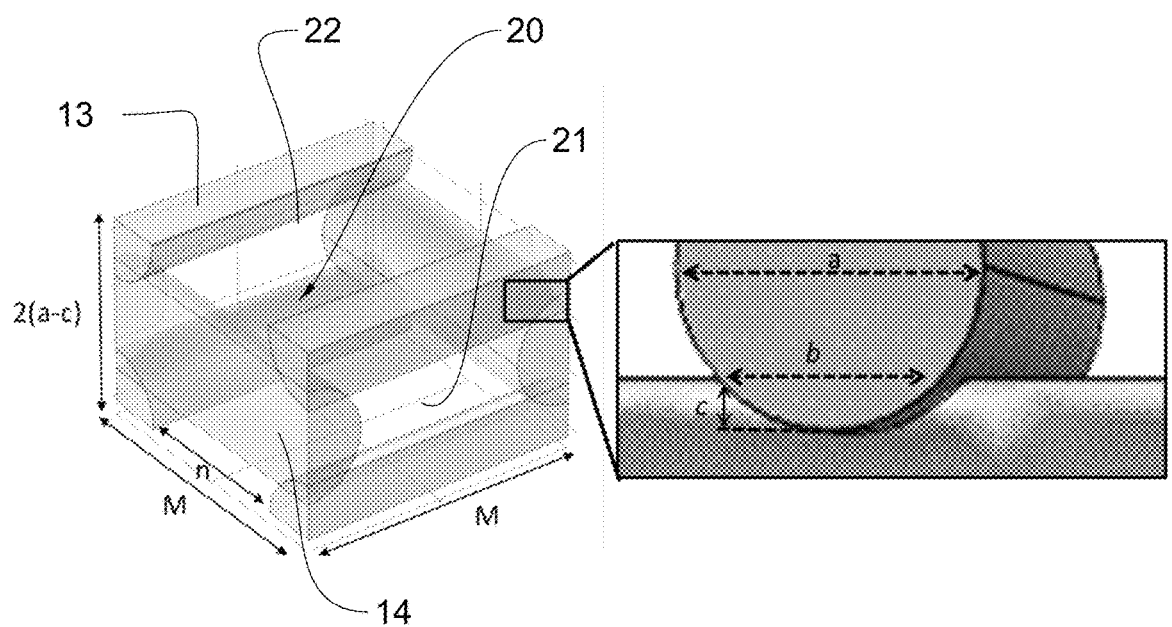
FIG. 2 represents a unit pore cell as defined in an orthogonal fibre disposition scheme, with fibres of consecutive layers being orthogonal to one another.

The local porosity can be determined based on the geometry of a unit pore cell 20 as shown and defined in FIG. 2. A pore can be regarded as a cell delimited on all sides by fibres 13, 14. The stacking factor c refers to the interpenetration depth between fibres of consecutive layers. The stacking factor is obtained, e.g. during build of a 3DFD structure but is analogous with other additive manufacturing processes, by increasing the (vertical) build height (z) by an amount less than the fibre diameter, when starting a new layer on top of the previous one. The fibre diameter can be determined by optical microscopy or Scanning Electron Microscope imaging of a cross-section of the material and is mainly determined by the nozzle diameter of the 3DFD apparatus, printing conditions and the shrinkage upon sintering. The stacking factor c may be influenced by the paste composition (e.g. viscosity), fibre thickness, inter-fibre distance and printing conditions such as temperature and humidity. The stacking factor has a strong influence on the mechanical strength of the fibres, but also influences the macroporosity and the interconnectivity of the macropores. The stacking factor c can be measured by means of a Scanning Electron Microscope imaging. Further, a=M−n is fibre diameter (mm), n is inter-fibre distance (mm) and M is axial centre spacing between two fibres (mm). The macroporosity (P, %) of the cell can be calculated as follows, with SSA being the specific surface area (SSA, mm$^2$/mm$^3$), $S_c$ is the loss of the surface area of two connected fibres (mm$^2$), $S_f$ is surface area of the two fibres (mm$^2$), $V_{cell}$ is the unit cell volume (mm$^3$) and $V_{fibre}$ is the fibre volume (mm$^3$):

$$b = 2\sqrt{2ac - c^2} \text{ (mm)} \quad \text{(Eq. 1)}$$
$$S_c = \frac{\pi a * b}{4} \text{ (mm}^2\text{)}$$
$$S_f = \pi M a \text{ (mm}^2\text{)}$$
$$V_{cell} = 2(a - c)M^2 \text{ (mm}^3\text{)}$$
$$V_{fibre} = \frac{\pi M a^2}{4} \text{ (mm}^3\text{)}$$
$$SSA = \frac{2(S_f - 2S_c)}{V_{cell}} \text{ (mm}^2\text{/mm}^3\text{)}$$
$$SSA = \frac{\pi a(M - \sqrt{2ac - c^2})}{M^2(a - c)} \text{ (mm}^2\text{/mm}^3\text{)}$$
$$P = \left(1 - \frac{2V_{fibre} - V_c}{V_{cell}}\right) * 100 \text{ (\%)}$$

with $V_c$ the volume of the intersection of two fibres with same fibre diameters a.

$V_c$ depends on the stacking factor c. The stacking factor c can be in the range 0≤c≤a. While c=a, $V_c$ is a "Steinmetz solid". Therefore, $$V_c = \frac{16}{3}\left(\frac{a}{2}\right)^3.$$

While c is 0<c<a, a circular cone volume can be assumed for simplifying the calculation of $V_c$, which is an approximation of the real elliptic cone volume. Assuming a circular cone volume:

$$V_c = 2V_{cones}$$
$$V_{cones} = 2\pi\left(\frac{b}{2}\right)^2\frac{c}{3}.$$

Reference to porosity in the present description relates to macroporosity, e.g. porosity between the fibres disregarding porosity of or within the fibres. Advantageously, macropores have a pore size of at least 10 µm in diameter, advantageously a pore size of at least 25 µm, advantageously at least 50 µm. Absolute (macro)porosity values in structures according to aspects of the disclosure are not particularly limiting. Advantageous values are between 40% and 95% porosity, advantageously between 50% and 80%. Average (macro)porosity values of porous structures according to present aspects are advantageously between 50% and 90%, advantageously between 55% and 85%, advantageously between 60% and 80%.

According to aspects of the disclosure, the difference (i.e. the change) in porosity (expressed as a percentage) between the first regions and the second regions is at least 4%, advantageously at least 5%, advantageously at least 6%, advantageously at least 8%, advantageously at least 10%. In other words, assuming the (volume) porosity is P1(%) in the first region (evaluated at the surface 111), and P2(%) in the second region (evaluated at the surface 111), the difference in porosity ΔP (%)=P1−P2. The porosity may change between a porosity between 50% and 95%, advantageously between 60% and 90%, advantageously between 70% and 90% in the first region and a porosity between 40% and 80%, advantageously between 50% and 70%, advantageously between 50% and 60% in the second region.

In porous (scaffold) structures according to aspects of the disclosure, the fibres advantageously have a diameter a in the range between 20 μm and 2 mm, advantageously between 40 μm and 1 mm, advantageously between 60 μm and 600 μm, with advantageous values being 80 μm, 100 μm, 150 μm, 200 μm, 300 μm, 400 μm, 500 μm. All fibres within a same layer of the structure typically have a same diameter, and the fibre diameter may be the same in all layers of the structure or may change between layers, e.g. by using different nozzles with different diameters for extruding the fibres.

The inter fibre distance n, e.g. within a same layer, may vary between 0 μm and 5 mm, and is advantageously between 10 μm and 2 mm, advantageously between 25 μm and 1 mm, advantageously between 50 μm and 900 μm, advantageously between 100 μm and 800 μm, and advantageously at least 200 μm, advantageously at least 300 μm. The inter fibre distance n typically changes within one layer so as to obtain a change in porosity, and advantageously to obtain a porosity gradient. In the scaffold structures described herein, the interfibre distance relates to the size of a pore cell 20.

The stacking factor c may vary between 0 and the fibre diameter a, advantageously 0.01a≤c≤0.99a, advantageously 0.02a≤c≤0.90a, advantageously 0.03a≤c≤0.50a, advantageously 0.05a≤c≤0.20a. Advantageously, the ratio c/a is at least 0.075, at least 0.1, at least 0.125, at least 0.15. The stacking factor typically is constant within one layer, and may change between layers. Typical values of the stacking factor c may range between 10 μm and 200 μm, advantageously between 20 μm and 150 μm, advantageously between 30 μm and 100 μm, e.g. 70 μm.

Referring to FIG. 2, the fibre diameter a and the stacking factor c define the size of the interconnection between adjacent pores within a same layer, also referred to as pore throat 21. The size of the pore throat 21, which may be defined as a-2c is advantageously at least 20 μm, advantageously at least 50 μm. The inter-fibre distance n and disposition of the fibres (e.g. staggered or aligned) mainly defines the size of the interconnection 22 between pores of consecutive layers. The pore interconnections 22 define paths in a direction perpendicular to the plane of the fibre layers, and therefore may define the pore interconnection in a direction of depth of the structure 11, starting from the external surface 111. The size of the pore interconnections 21 and/or 22 relates to the pore interconnectivity and may be important for the first regions with higher porosity to promote bone ingrowth, or for the second regions with smaller porosity to promote vascularisation, and may be important for both regions. Typically, the size of the pore interconnections 22, may be larger for the first regions and smaller for the second regions. Possibly, the first regions and the second regions may have different pore interconnection sizes.

Additive manufacturing techniques allow for easily and effectively making monolithic structures with desired porosity gradients. For porous structures built up out of an arrangement of fibres, the easiest way of obtaining a porosity gradient is through changing the spacing between (parallel) fibres within some or all layers, i.e. the inter fibre distance n. One example is shown in FIG. 1 showing the disposition of the fibres 13, 14 as seen from a direction orthogonal to the planes of the (parallel) layers. In FIG. 1, the fibres 13 within a same layer are disposed parallel to one another and the fibres 13 and 14 of consecutive layers are transverse, e.g. orthogonal to one another. It can be observed that in the first regions 112, the spacing (interfibre distance $n_1$) between adjacent fibres is larger as compared to the interfibre distance ($n_2$) of the structure in the second regions 113. This change in the interfibre distance (or, in more general terms, the spacing between adjacent fibres) can be applied to all layers, or alternatively to some but not all the layers, e.g. only layers having fibres parallel to fibres 13, to obtain a porosity change or gradient.

Figure 3:
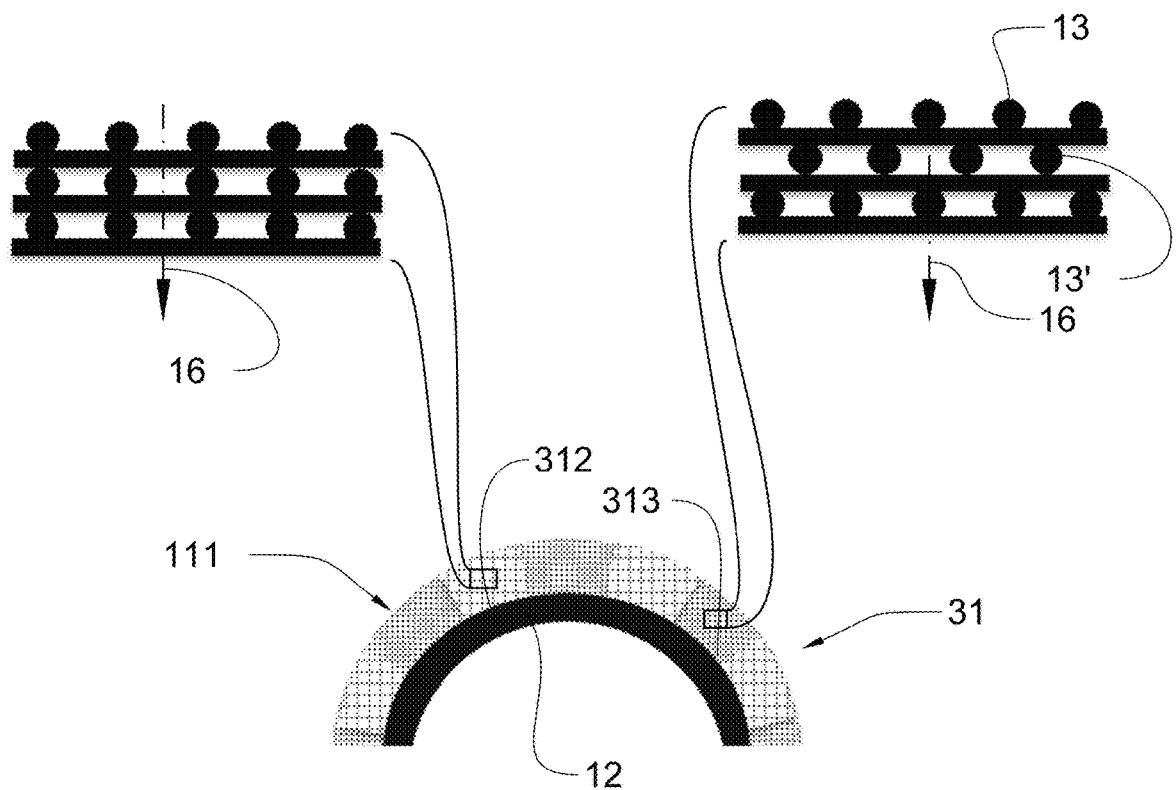
FIG. 3 represents a cross sectional view of an example surgical implant according to an alternative aspect of the disclosure, wherein different regions have different pore interconnectivity in a direction of build of the porous structure.

In addition, or alternatively to a porosity difference on the surface 111, the first regions and the second regions may have different pore interconnectivity between consecutive layers, as shown in FIG. 3. The scaffold structure 31 of FIG. 3 comprises first regions 312 and second regions 313 having different pore interconnectivity in the direction 16 perpendicular to the fibre layers. This may be obtained by staggering the fibres 13 and 13' in different layers. Even though in this example the size of a unit pore cell remains the same between the first region 312 and the second region 313 due to identical interfibre distance, the pore cells in second regions 313 are staggered, which reduces the pore interconnectivity between adjacent layers. It will be convenient to note that a change in pore interconnectivity such as shown in the example of FIG. 3 can be combined with the change in porosity such as shown in the example of FIG. 1.

Figure 4:
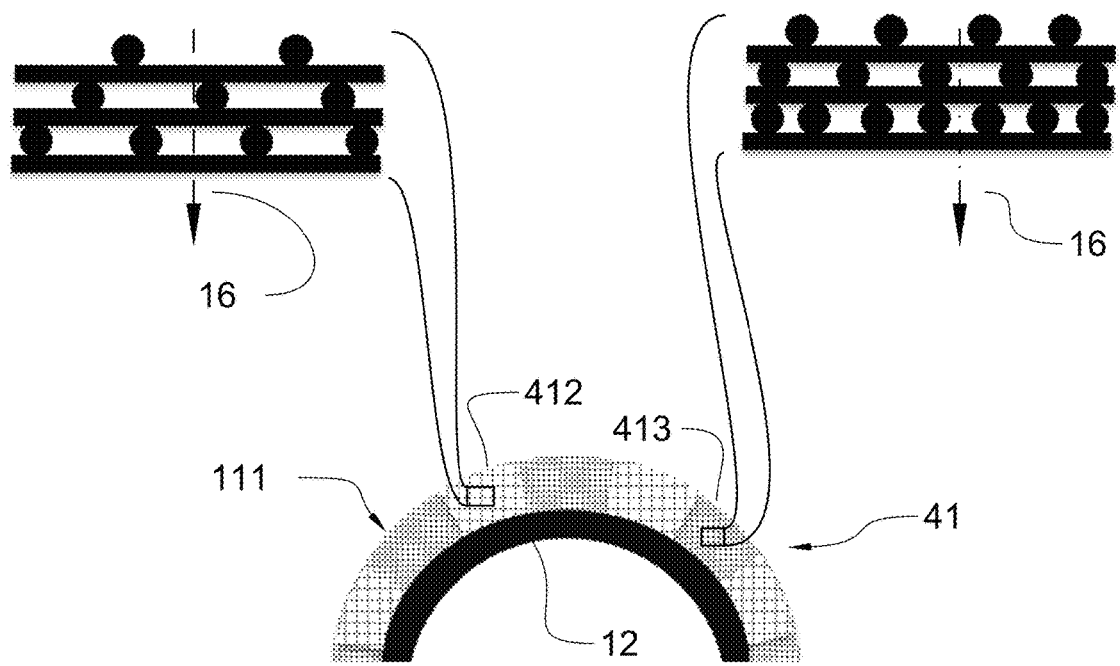
FIG. 4 represents a cross sectional view of an example surgical implant as in FIG. 1, in which additionally a porosity gradient is applied in a direction of build of the layers by changing the inter-fibre distance.

Referring to FIG. 4, a scaffold structure 41 is shown which differs from the structure 11 of FIG. 1 in that in the first regions 412 and in the second regions 413 a porosity gradient is applied in the structure 41 along a direction 16 of approach to, or away from, the surface 111, i.e. a direction of approach to the dense part 12. This porosity gradient is applied in addition to the change in porosity between first regions 412 and second regions 413. In the example shown, the porosity gradient is obtained by changing the interfibre distance n, e.g. increasing n towards the external surface 111 to obtain a higher porosity at or near the surface 111 and a lower porosity towards the dense part 12. It will be convenient to note that such a porosity gradient can be applied to only one of the first regions 412 and the second regions 413, or alternatively to both.

Figure 5:
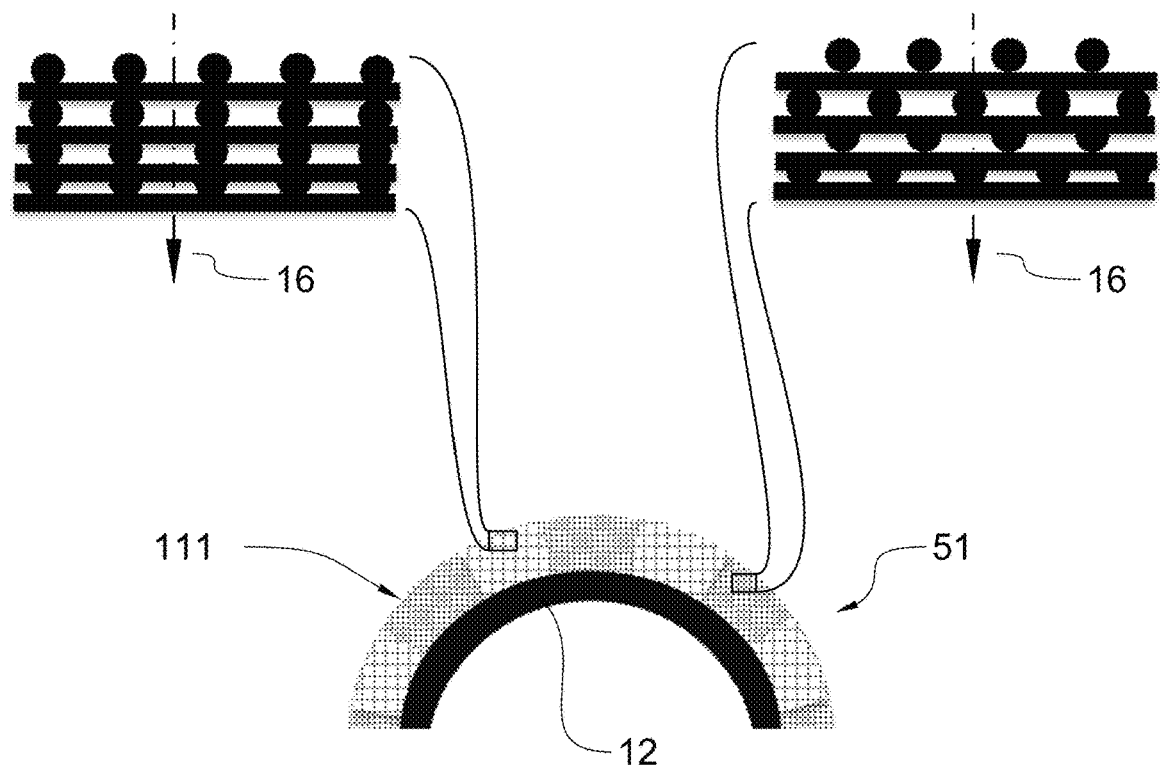
FIG. 5 represents a cross sectional view of an example surgical implant as in FIG. 4, in which additionally the stacking factor is changed through the layers in the direction of the porosity gradient.

Referring to FIG. 5, a scaffold structure 51 is shown which differs from the structure 41 of FIG. 4 in that the porosity gradient along direction 16 is (further) obtained by changing the stacking factor c through the layers in the stack of structure 51. In the example, c is increased from the external surface 111 towards the dense part 12. Changing the porosity by changing the stacking factor can be applied in addition to, or in the alternative of changing the interfibre distance.

Figure 6:
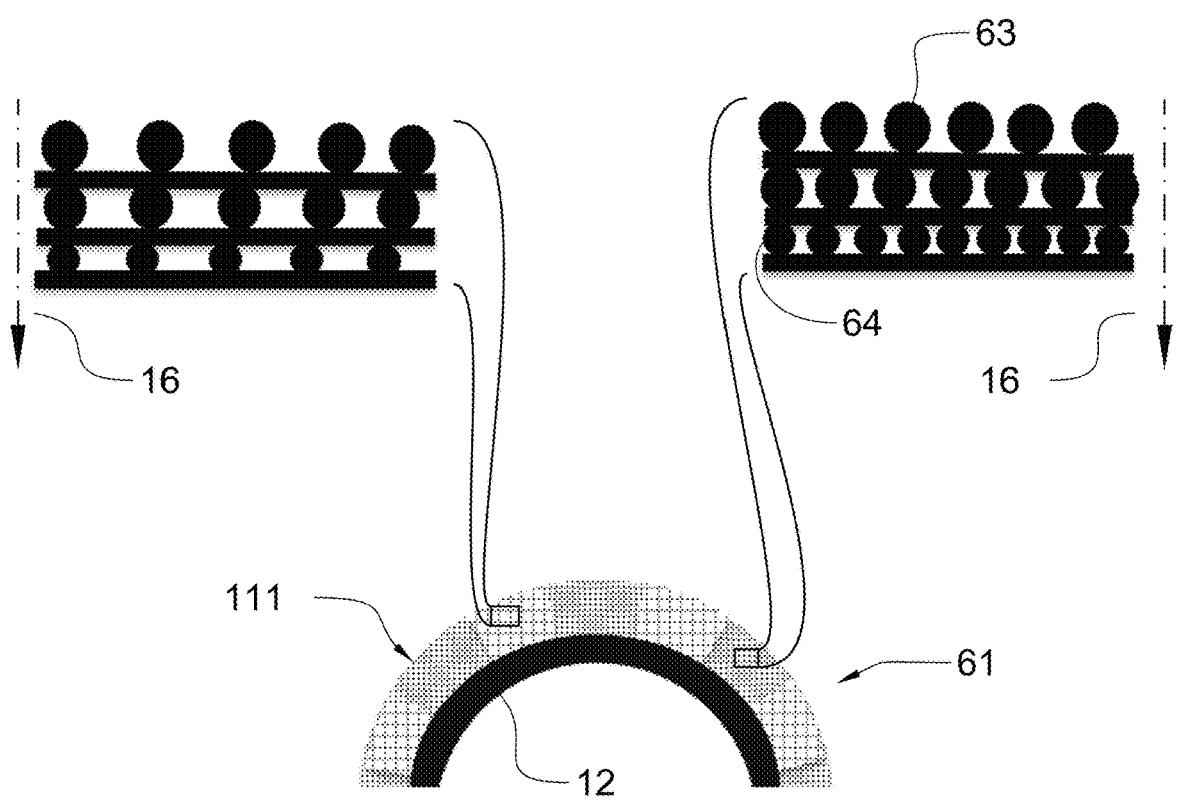
FIG. 6 represents a cross sectional view of an example surgical implant which differs from the implant of FIG. 4 in that the porosity gradient is obtained by a change of fibre diameter between layers.

Referring to FIG. 6, a scaffold structure 61 is shown which differs from the structure 41 of FIG. 4 in that the porosity gradient along direction 16 is obtained by a change of the fibre diameter through different layers. Layers proximal to the external surface 111 may comprise fibres 63 having a larger diameter compared to fibres 64 arranged in layers remote from the surface 111. Alternatively, layers proximal to surface 111 may comprise fibres having a smaller diameter compared to fibres of layers remote from surface 111. In the latter case, a porosity gradient may be obtained by appropriate selection of the inter fibre distance n in each layer, e.g. with n decreasing in the direction 16. The change of fibre diameter as described hereinabove may be combined with other ways of obtaining a porosity gradient in direction 16, such as those described in relation to FIG. 4 or 5.

Figure 7:
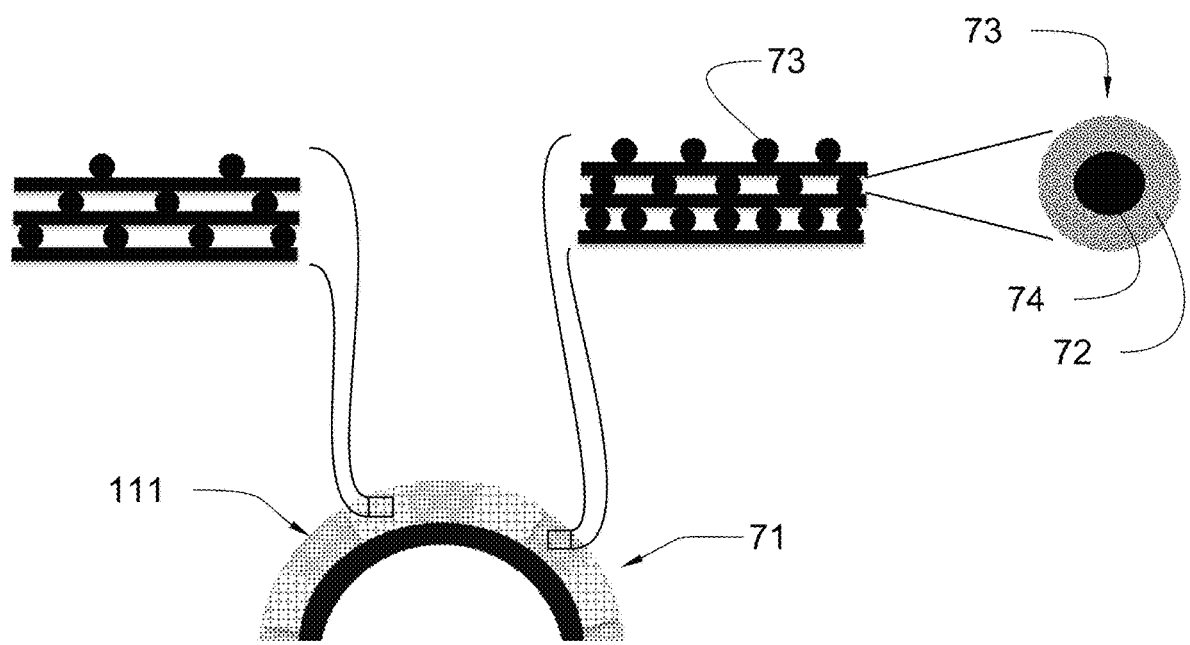
FIG. 7 represents a cross sectional view of an example surgical implant which differs from the implant of FIG. 4 in that the fibres are microporous.

It will be convenient to note that the fibres themselves may comprise a microporosity, e.g. porosity with pore size smaller than the size of the macropores as indicated above, as shown in FIG. 7. The scaffold structure 71 of FIG. 7 differs from the structure 41 of FIG. 4 in that the fibres comprise a microporosity. The microporosity may extend in a peripheral region, e.g. sheath 72, of the fibres 73. In this case, the fibres 73 may comprise a dense core 74. Alternatively, fibres 73 may be microporous throughout.

Microporous fibres may be obtained by subjecting the fibres to a phase inversion process as e.g. described in WO 2009/027525, 5 Mar. 2009, which is incorporated herein by reference. Biomedical implants with macro- and microporous structure may stimulate osseointegration and provide sufficient local mechanical strength for fixation/implantation. Due to the macroporosity, the implant materials can be easily coated with conventional coating procedures such as dip-coating or wash-coating, with growth factors. Due to the microporosity, the as such deposited coatings will have a much better adhesion. Advantageously, the (microporous) fibres are otherwise solid fibres, i.e. they are advantageously not hollow.

The microporous fibre or filament morphology may be induced by phase inversion. A method for producing such morphology may comprise the steps of:
a) preparing a suspension comprising particles of a predetermined material, a liquid solvent, one or more binders and optionally one or more dispersants,
b) depositing said suspension in the form of fibres or filaments in a layered fashion, e.g. according to a predetermined disposition of fibres or filaments, thereby creating a porous structure,
c) inducing phase inversion, whereby said filaments are transformed from a liquid to a solid state, by exposing said filaments during the deposition of the filaments to a non-solvent vapour and to a liquid non-solvent,
d) thermally treating the structure of step c) by calcining and sintering said structure.

In other words, step c) of the present method involves the step of exposing the filaments during the deposition of the filaments to a non-solvent vapour and to a liquid non-solvent, such that the deposited filaments solidify and obtain surface roughness and microporosity. In a preferred embodiment, step b) is carried out in a non-solvent environment.

Advantageously, an alternative step c) comprises the step of c1) bringing the filaments during the deposition of the filaments into contact with a non-solvent vapour, and the step of c2) immersing the structure of step c1) in a liquid non-solvent, thereby creating a filament-based porous structure having suitable filament morphology. Phase inversion can be completed in a next step (step c2) of the present method by immersing the structure in a liquid non-solvent.

The fibres or filaments in the sintered porous structure obtained after step d) advantageously comprise an average surface roughness (Ra) which is higher than 4 μm. Moreover, the filaments in the sintered porous structure obtained after step d) also have a microporosity (after sintering) comprised between 1 and 50%, preferably between 5 and 30%. Microporosity refers to a porosity wherein the pores have a size smaller than macropores as indicated above.

Figure 8:
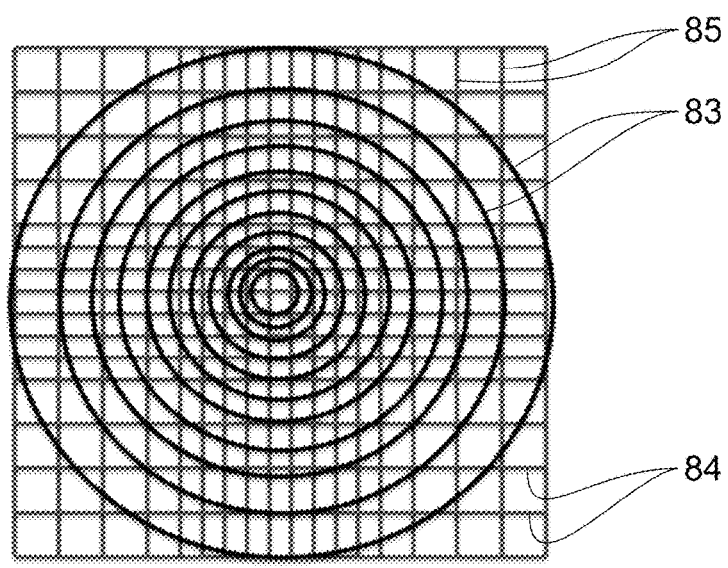
FIG. 8 represents an example fibre arrangement pattern as seen from a direction perpendicular to the plane of the layers in which the fibres are arranged.

Referring to FIG. 8, a possible arrangement of fibres is shown. This arrangement is particularly suited as scaffold structure for the acetabular component indicated above. The structure 81 comprises a repeating pattern of three consecutive layers. In a first layer, fibres 83 are arranged in concentric circles. A second layer comprises fibres 84 arranged parallel to one another. A third layer comprises fibres 85 arranged parallel to one another. Fibres 85 are perpendicular to the fibres 84 of the second layer. The porosity difference between different regions or areas in structure 81 can be brought about by changing the inter-fibre distance in one, some or all three layers. As shown in FIG. 8, the in the fibre distance is changed in each one of the three layers in a graded way to obtain different regions with different porosity. It will be convenient to note that the first, second and third layer may be arranged in any order.

The materials of which the porous structures according to aspects of the present disclosure are made include metals, ceramics, and composite materials, in particular those materials being biocompatible.

The present disclosure may include one or more of the following concepts:

A. A surgical implant (10), comprising a porous structure (11) with interconnected pores (20) for ingrowth of bone into the porous structure, wherein the porous structure comprises an arrangement of fibres (13, 14) which are attached to one another, wherein the fibres are arranged in layers (151, 152, 153), the layers being stacked, characterised in that the porous structure comprises a surface (111), wherein the surface comprises different regions (112, 113) having different porosities, the different porosities being determined by the arrangement of fibres.

B. The surgical implant of paragraph A, wherein the porous structure (11) is attached to a dense part (12), and wherein the surface is located opposite the dense part.

C. The surgical implant of paragraph B, wherein the dense part comprises an interface (115) with the porous structure, wherein a direction (16) of stacking of the layers of the porous structure is oriented in a direction of approach to, or away from the interface.

D. The surgical implant of any one of the preceding paragraphs, wherein the surface comprises a first porosity in a first region (112) on the surface and a second porosity in a second region (113) on the surface, the difference between the first porosity and the second porosity being at least 4%.

E. The surgical implant of paragraph D, wherein the difference between the first porosity and the second porosity is at least 6%.

F. The surgical implant of paragraph D or E, wherein the first porosity is between 45% and 90% and wherein the second porosity is between 40% and 85%.

G. The surgical implant of paragraph F, wherein the first porosity is between 70% and 90% and wherein the second porosity is between 40% and 60%.

H. The surgical implant of any one of the preceding paragraphs, wherein the porous structure has an average porosity between 50% and 80%.

J. The surgical implant of any one of the preceding paragraphs, wherein the fibres (13, 14) have a diameter between 20 μm and 5 mm.

K. The surgical implant of any one of the preceding paragraphs, wherein fibres of consecutive layers interpenetrate, wherein a ratio between a penetration depth (c) between the fibres of the consecutive layers and a diameter (a) of the fibres is between 0.05 and 0.5.

L. The surgical implant of paragraph K, wherein the ratio is between 0.1 and 0.5.

M. The surgical implant of any one of the preceding paragraphs, wherein a spacing (n) between adjacent fibres of a same layer is between 10 μm and 5 mm.

N. The surgical implant of paragraph M, wherein the spacing (n) between the fibres in at least one layer changes between the first region and the second region to obtain the different porosities.
O. The surgical implant of any one of the preceding paragraphs, wherein the porous structure comprises a porosity gradient in a direction (16) orthogonal to the surface (111).
P. The surgical implant of any one of the preceding paragraphs, wherein the porous structure (11) is attached to a dense part (12), wherein the surface is located opposite an interface (115) of the porous structure with the dense part, and wherein the porous structure comprises a porosity gradient wherein the porosity decreases in a direction (16) of approach to the dense part.
Q. The surgical implant of paragraph O or P, wherein a penetration depth (c) between the fibres of consecutive layers changes along a direction of the porosity gradient.
R. The surgical implant of any one of the preceding paragraphs, wherein the fibres comprise micropores.
S. The surgical implant of any one of the preceding paragraphs, wherein the different regions (112, 113) having different porosities alternate on the surface.
T. A method of making a surgical implant (10), comprising forming fibres (13, 14) in layers, the layers being stacked; connecting the fibres of consecutive layers to one another to obtain a porous structure (11); characterised in that the method comprises the step of arranging the fibres in proximity of a surface (111) of the porous structure with different interspaces in different regions of the surface such that the different regions (112, 113) have different porosities.
U. The method of paragraph T, comprising making a dense part and attaching the porous structure to the dense part.

The invention claimed is:

1. A surgical implant, comprising: a porous structure having interconnected pores configured for ingrowth of bone into the porous structure, wherein the porous structure comprises an arrangement of fibers which are attached to one another, wherein the fibers are arranged in layers, and wherein the layers are stacked; and wherein the porous structure includes a surface including a plurality of regions having different porosities, the different porosities being determined by the arrangement of fibers; and wherein the porous structure is attached to a dense part, and wherein the surface is disposed opposite the dense part, such that each of the regions having different porosities extend from the surface toward the dense part.

2. The surgical implant of claim 1, wherein the dense part includes an interface with the porous structure, wherein a direction of stacking of the layers of the porous structure is oriented along a direction of approach to the interface or a direction away from the interface.

3. The surgical implant of claim 1, wherein the surface has a first porosity in a first region of the surface and a second porosity in a second region of the surface, a difference between the first porosity and the second porosity being at least 4%.

4. The surgical implant of claim 3, wherein the difference between the first porosity and the second porosity is at least 6%.

5. The surgical implant of claim 3, wherein the first porosity is between 45% and 90% and wherein the second porosity is between 40% and 85%.

6. The surgical implant of claim 5, wherein the first porosity is between 70% and 90% and wherein the second porosity is between 40% and 60%.

7. The surgical implant of claim 1, wherein the porous structure has an average porosity between 50% and 80%.

8. The surgical implant of claim 1, wherein the fibers each have a diameter between 20 µm and 5 mm.

9. The surgical implant of claim 1, wherein fibers of consecutive layers interpenetrate, wherein a ratio between a penetration depth between the fibers of consecutive layers and a diameter of the fibers is between 0.05 and 0.5.

10. The surgical implant of claim 9, wherein the ratio is between 0.1 and 0.5.

11. The surgical implant of claim 1, wherein a spacing between adjacent fibers of a same layer is between 10 µm and 5 mm.

12. The surgical implant of claim 11, wherein the spacing between the fibers in at least one layer changes between a first region and a second region to obtain the different porosities.

13. The surgical implant of claim 1, wherein the porous structure comprises a porosity gradient in a direction orthogonal to the surface.

14. The surgical implant of claim 1, wherein the porous structure comprises a porosity gradient wherein the porosity decreases in a direction of approach to the dense part.

15. The surgical implant of claim 13, wherein a penetration depth between the fibers of consecutive layers changes along a direction of the porosity gradient.

16. The surgical implant of claim 1, wherein the fibers comprise micropores.

17. The surgical implant of claim 1, wherein the different regions having different porosities alternate on the surface.

18. The surgical implant of claim 1, wherein each of the regions having different porosities extend from the surface to the dense part through a depth of the porous structure.

* * * * *